(12) United States Patent
Grayzel et al.

(10) Patent No.: US 8,690,904 B2
(45) Date of Patent: Apr. 8, 2014

(54) PERCUTANEOUS ACCESS CONDUIT

(76) Inventors: Jeffrey Grayzel, Morristown, NJ (US);
Joseph Grayzel, Englewood, NJ (US);
William Allen, Houston, TX (US); Fred Karl, Westling, OR (US); Alan Bachman, Milford, CT (US); Ray Adams, Ansonia, CT (US)

( * ) Notice: Subject to any disclaimer, the term of this patent is extended or adjusted under 35 U.S.C. 154(b) by 860 days.

(21) Appl. No.: 11/893,853

(22) Filed: Aug. 18, 2007

(65) Prior Publication Data

US 2007/0288046 A1 Dec. 13, 2007

Related U.S. Application Data

(60) Continuation of application No. 10/862,905, filed on Jun. 7, 2004, now Pat. No. 7,666,201, which is a division of application No. 10/030,216, filed as application No. PCT/US00/24684 on Sep. 8, 2000, now Pat. No. 6,761,725.

(60) Provisional application No. 60/152,745, filed on Sep. 8, 1999.

(51) Int. Cl.
*A61B 17/32* (2006.01)
*A61F 11/00* (2006.01)

(52) U.S. Cl.
USPC .......................................... 606/174; 606/108

(58) Field of Classification Search
USPC ......... 606/108, 205–211, 167–185, 190–199, 606/213; 604/164, 264, 142
See application file for complete search history.

(56) References Cited

U.S. PATENT DOCUMENTS

| | | | |
|---|---|---|---|
| 2,191 A | 7/1841 | Pitney | |
| 1,214,562 A | 2/1917 | McGrath | |
| 2,669,993 A | 2/1954 | Curutchet | |
| 2,846,766 A | 8/1958 | Harter | |
| 2,994,321 A * | 8/1961 | Tischler | ........................ 606/207 |
| 2,996,044 A | 8/1961 | Parker | |

(Continued)

FOREIGN PATENT DOCUMENTS

| | | |
|---|---|---|
| DE | 4115548 | 11/1991 |
| FR | 2596272 | 10/1987 |

(Continued)

OTHER PUBLICATIONS

Supplementary Partial European Search Report for European Application No. 00961686.3 dated May 14, 2007.

(Continued)

*Primary Examiner* — Darwin Erezo
*Assistant Examiner* — Katrina Stransky

(57) ABSTRACT

A tubular conduit is used to access blood vessels or other structures in the human body. The conduit has a distal tip angled to match the angle of entry into the body and an end contour adapted for the surface of the target vessel or organ. The contour may be curved to match the curve on the outer surface of the vessel or organ. The conduit's angled and contoured distal end may be adapted to engage, and align the conduit with, the surface of the vessel or organ. The conduit bears a longitudinal groove along its lower, inner surface. When the conduit is appropriately aligned, the groove may be used to guide a needle tip to the desired location, for example, the mid-line of the vessel or organ.

59 Claims, 11 Drawing Sheets

(56) References Cited

U.S. PATENT DOCUMENTS

| | | | |
|---|---|---|---|
| 3,720,235 A * | 3/1973 | Schrock | 138/137 |
| D231,034 S | 3/1974 | Moore | |
| 3,844,274 A | 10/1974 | Nordstrom | |
| D239,910 S | 5/1976 | Megna | |
| 3,980,086 A | 9/1976 | Kletschka et al. | |
| 3,987,542 A | 10/1976 | Visco | |
| 4,049,002 A | 9/1977 | Kletschka et al. | |
| 4,088,134 A * | 5/1978 | Mazzariello | 606/207 |
| 4,140,124 A | 2/1979 | Curutchet | |
| 4,226,240 A * | 10/1980 | Walker, Jr. | 606/207 |
| D258,714 S | 3/1981 | Backstrom | |
| 4,760,848 A | 8/1988 | Hasson | |
| 4,819,636 A | 4/1989 | Gerich et al. | |
| 4,889,112 A | 12/1989 | Schachner et al. | |
| D310,714 S | 9/1990 | Dolwick | |
| 5,026,385 A | 6/1991 | Schutte et al. | |
| D318,780 S | 8/1991 | Bendickson et al. | |
| D331,179 S | 11/1992 | Omichi | |
| 5,224,931 A | 7/1993 | Kumar | |
| 5,234,460 A | 8/1993 | Stouder | |
| 5,356,408 A | 10/1994 | Rydell | |
| 5,470,162 A | 11/1995 | Rubin | |
| 5,484,434 A | 1/1996 | Cartmell et al. | |
| 5,540,662 A | 7/1996 | Nicholson | |
| 5,632,746 A | 5/1997 | Middleman et al. | |
| 5,643,293 A * | 7/1997 | Kogasaka et al. | 606/148 |
| 5,643,318 A * | 7/1997 | Tsukernik et al. | 606/214 |
| 5,693,069 A * | 12/1997 | Shallman | 606/205 |
| 5,746,755 A * | 5/1998 | Wood et al. | 606/148 |
| 5,772,670 A | 6/1998 | Brosa | |
| D396,057 S | 7/1998 | Bistrack | |
| 5,797,939 A | 8/1998 | Yoon | |
| 5,843,124 A | 12/1998 | Hammerslag | |
| 6,004,341 A | 12/1999 | Zhu et al. | |
| 6,009,600 A | 1/2000 | Egeland et al. | |
| 6,036,385 A | 3/2000 | Bistrack | |
| 6,063,088 A * | 5/2000 | Winslow | 606/86 A |
| 6,099,550 A | 8/2000 | Yoon et al. | |
| 6,117,145 A | 9/2000 | Wood et al. | |
| 6,254,293 B1 | 7/2001 | Citrenbaum | |
| 6,315,476 B2 | 11/2001 | Nakagawa | |
| 6,361,541 B1 * | 3/2002 | Barnhart | 606/108 |
| 6,371,968 B1 * | 4/2002 | Kogasaka et al. | 606/190 |
| 6,425,901 B1 * | 7/2002 | Zhu et al. | 606/142 |
| 6,929,606 B2 * | 8/2005 | Ritland | 600/201 |
| 6,964,675 B2 | 11/2005 | Zhu et al. | |
| 2004/0097999 A1 | 5/2004 | Wilson | |
| 2004/0098039 A1 | 5/2004 | Sinding | |
| 2004/0221425 A1 | 11/2004 | Lawless | |

FOREIGN PATENT DOCUMENTS

| | | |
|---|---|---|
| WO | 95/13023 | 5/1995 |
| WO | 98/24374 | 6/1998 |
| WO | 99/62405 | 12/1999 |

OTHER PUBLICATIONS

International Search Report for PCT/US00/24684 dated Mar. 22, 2001.

\* cited by examiner

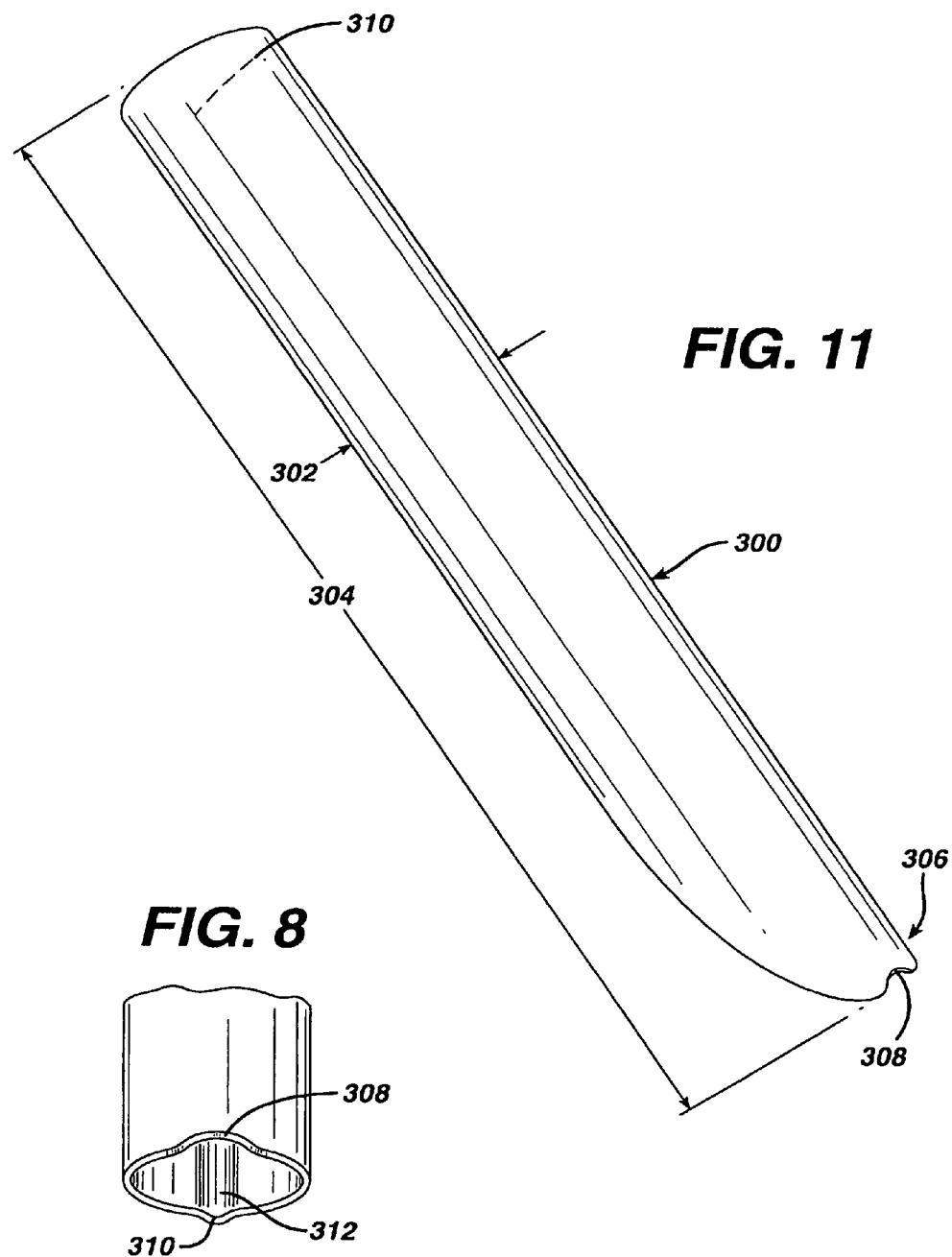

PERCUTANEOUS ACCESS CONDUIT

This application is a continuation of and claims the benefit of U.S. patent application Ser. No. 10/862,905 (now U.S. Pat. No. 7,666,201) filed Jun. 7, 2004 which is a divisional of U.S. patent application Ser. No. 10/030,216 (now U.S. Pat. No. 6,761,725), filed Sep. 3, 2002, which is filed under 35 U.S.C. §371 from Appl. No. PCT/US00/24684, filed Sep. 8, 2000, which claims the benefit of U.S. Prov. Appl. No. 60/152,745, filed Sep. 8, 1999. U.S. patent application Ser. No. 10/862,905, filed Jun. 7, 2004, is hereby incorporated by reference in its entirety.

BACKGROUND OF THE INVENTION

1. Field of the Invention

The present invention relates to medical procedures and instruments, and more particularly to apparatus and methods for dissection of tissue from skin to an underlying blood vessel or body structure, and the methods of accomplishing such dissections and arterial and venous punctures.

2. Description of the Prior Art

Present surgical practice for percutaneous puncture of the femoral artery with entry into the arterial lumen is a blind approach. The same is true for other arteries and veins accessible via the skin. These procedures have become ever more common and are frequent during procedures relating to invasive cardiology, invasive radiology, and cardiac surgery.

Currently, puncture of a femoral artery is accomplished by first feeling the pulse through the skin and underlying tissue; a trajectory or path for the needle is thereby estimated by the practitioner to properly engage the artery. The needle is then advanced toward the artery through the skin, and it is hoped that the needle will puncture the artery in its mid-line, which is optimal. However, often the needle will puncture the artery in an off-center position, or the artery may be missed entirely, and multiple attempts executed before success. Further, if the artery is punctured off-center this is not evident. Thus, in general, the quality of the puncture is not known.

An off-center puncture makes insertion of the catheter more difficult and increases the likelihood of arterial trauma and tearing of the vessel wall, resulting in more difficult hemostasis at the end of the procedure. Many factors interfere with a successful mid-line puncture, leading to an off-center puncture or missing the artery entirely. Subcutaneous tissue, particularly if fibrous, may deflect the needle from its intended path. Thicker subcutaneous tissue, as found in obese persons, increases the difficulty of accurately assuming the trajectory of the needle and resulting puncture of the artery, as well as depriving the operator of feeling that the puncture is actually occurring. Additionally, it must be estimated as to when the needle has actually entered the artery. Hence, many operators may push the needle through the rear wall without realizing that this has occurred.

Because of the uncertainty as to the location of the intersection of the needle with the artery and entry of the needle tip into the true lumen of the artery, many operators will intentionally push the needle to a greater depth so that the rear wall is also punctured (double-wall puncture), and then withdraw the needle slowly while awaiting the pulse of blood through the needle's open channel to indicate that the tip of the needle now lies inside the arterial lumen.

The difficulties enumerated above with respect to percutaneous vascular puncture are exacerbated when attempting a venous puncture, since pronounced pulsations to define the vessel are absent, and venous walls are thinner, hence more easily damaged. Also, venous entry (e.g. jugular, subclavian) relies heavily on superficial anatomic landmarks, which are less precise.

Percutaneous entry of a blood vessel is facilitated by instruments or apparatus that dissect a channel or path from skin to vessel, thereby eliminating tissue resistance to guidewires, catheters, or other implements. The geometry of contemporary instruments is such that the handles of the instrument, as held by the operator, and the joint of the instrument obstruct and prevent a clear view of the tips and the pathway they are creating.

It is important that a dissecting instrument provide a clear, unobstructed view of the dissecting tips and the channel created therefrom. For a dissecting instrument to provide such visualization of the subcutaneous channel and the underlying blood vessel, the gripping handles must be offset from the dissecting blades or fingers in such a way as to provide a direct and clear line of sight down to the tips of the instrument and hence an unobstructed view of the surgical site. Additionally, the channel created by the fingers must be broad enough for visualization to occur.

Another problem associated with percutaneous entry into a blood vessel is the bleeding that results. After the needle is removed and/or any other invasive removed from the blood vessel, it is necessary to close the general area of the entry on the vessel. This, however, is not a completely successful method of preventing the bleeding. Since the pressure is applied externally on a relatively large area, there is always seepage resulting in bruising or even the buildup of adhesions from the internal blood.

Numerous surgical implements have been developed which would be useful in connection with the procedures to be accomplished by the present invention. However, none of these tools show or disclose configurations which meet the requirements for the procedures as set forth in the present invention. Some of the prior patents dealing with this subject matter are as follows.

U.S. Pat. No. 5,797,939 to Yoon discloses an endoscopic scissor. Note that the finger loops of the handle are at an angle to the main shaft, and that they are spread when the cutting blades are open, and also spread when the cutting blades are closed. (See FIG. 3). Additionally, the cylindrical tubular section of the device allows for passage of accessories to the end of the blades.

U.S. Pat. No. 5,356,408 to Rydell discloses a bipolar electrosurgical scissor instrument in which the handles are offset at 90 degrees and remain in an apparently open position when the blade itself is closed. Additionally, the blades are bent at an angle to the linear axis of the device to provide for an unobstructed view of the cutting area.

U.S. Pat. No. 5,153,997 to Chiavaras et al. discloses ergonomic scissors in which the finger grips are at right angles to the blade.

U.S. Pat. No. 4,889,112 to Schachner et al discloses a tracheostomy enlarging tool, which has offset probing fingers 107 and 108. These fingers have passage means in them to surround a wire which has been inserted into the trachea to guide the fingers into the trachea so that the passage into the trachea can be enlarged to widen the opening.

U.S. Pat. No. 4,819,636 to Gerich et al discloses a device for cutting and squeezing tubing, in which the finger mounts and the handles are offset from the cutting blades or working arms of the instrument.

U.S. Pat. No. 4,140,124 to Curutchet discloses a surgical instrument having an offset handle with special means for holding the thumb and the fingers in a ergonomic position. This patent does not have the same orientation of the handles as does the present invention.

U.S. Pat. No. 4,049,002 to Kletschka et al. discloses various scissors or clamps having fluid passages in the handles to allow fluid to be directed towards the tip of the implement. However, note that the passages are internal and are not used to coact with each other to form a cylindrical pathway between the blades.

U.S. Pat. No. 3,987,542 to Visco discloses scissors with off-set handles. Additionally, although not for the same purpose, the blades of the scissors have tubular sections. These are more for strength than for any functional purpose.

U.S. Pat. No. 1,214,562 to McGrath discloses lawn power sheers, which has off-set blades to the body portions 14 of the levers.

U.S. Pat. No. 331,179 DES to Omichi discloses hair-cutting scissors with a curved blade.

U.S. Pat. No. 310,714 DES to Dolwick discloses a surgical or dental scissors having the finger loops bent at an angle from the main shaft of the device and having the blade portions bent similarly to form another angle so as to make the device a double curved instrument with the handles somewhat parallel to the blades and the main shaft at an angle to both.

U.S. Pat. No. 258,714 DES to Backstrom discloses nail scissors having curved cutting blades.

U.S. Pat. No. 239,910 to Megna discloses scissors having bent finger loops.

U.S. Pat. No. 231,034 DES to Moore discloses a surgical clamp with bent fingers.

U.S. Pat. No. 2,191 to Pitney discloses a speculum having fingers AA which coact with the handle BB for spreading. FIG. 2 shows a levator, which is used to examine the anus once the fingers AA of the speculum are inserted.

OBJECTS AND SUMMARY OF THE INVENTION

Accordingly, to achieve the desired visualization of the operative site and the proper positioning of the needle to achieve the most effective puncture of a vessel, the present invention sets forth several coacting combinations of coacting instruments, some capable of independent action, as well as enabling clear visualization of the operative area, precise location of the operative site, capture and immobilization of the vessel, and guidance in the positioning and insertion of the puncturing needle.

Visualization of the operative area is accomplished by means of a dissecting-retracting tool with the hand-gripping and controlling members of the tool offset in two dimensions from angled blunt dissecting fingers to create a subcutaneous path from skin to vessel, providing a clear line of sight through the dissecting fingers to their very tips. Once visualized that dissection has occurred, conduit and obturator/carrier assemblies are matingly positioned within the blunt dissecting fingers to register with the ends of the dissecting fingers at the site of the blood vessel. The terminal ends of the conduit and obturator are angled and concavely shaped to conform to the vessel, and center the assembly on top of the vessel to be punctured. The dissector-retractor is removed and the obturator is then removed leaving the conduit in place and thus providing an open channel from skin to vessel surface. The conduit bears along its lower, inner surface a fine longitudinal groove capable of guiding a needle tip to the center of the blood vessel or, alternatively, guiding a light probe to illuminate the puncture site. This light probe along its upper surface carries a fine longitudinal groove that is also capable of guiding the needle to the center of the blood vessel. The light probe is centered within the conduit by mating a raised ridge along the longitudinal axis on the underside of the probe with the longitudinal groove located on the surface of the conduit. Centering of the illumination probe on the vessel is facilitated by a forked tip which captures the blood vessel equally on either side of the midline of the probe, and in the case of an artery, transmits arterial pulsations in a manner that enables the operator to feel that the illumination probe has captured and is centered on such artery.

Additionally, apparatus is provided for the placement of a sponge directly on the entry wound in the vessel. A sponge is positioned within the conduit and a sponge pusher pushes the sponge to the site of the entry where pressure is applied by the pusher directly on the sponge at the site of entry to reduce the bleeding upon removal of the invasive items from the vessel.

These features facilitate a preferred single-wall puncture of the vessel and discourage the more harmful double-wall puncture.

The present invention also sets forth a method for vascular puncture and more particularly for the arterial puncture procedure. The operator begins by palpating an artery, such as the femoral artery. The line of maximal pulsation is ascertained, and a small incision in the skin is made. A dissecting-retracting tool is then employed to create a skin-to-vessel channel until the vessel to be punctured is reached. The tips of the dissecting-retracting tool then rest upon the vessel to be punctured, the blood vessel is palpated, and the fingers are spread into an open position by squeezing the handles toward one another. The vessel is inspected through the spread fingers. A tubular access conduit, mounted on an obturator/carrier, is inserted and advanced until it is positioned by the contoured ends of the conduit and obturator resting upon the artery with the concavity matching the radial curvature of the vessel. The dissector-retractor is removed over the obturator leaving the obturator and conduit in place. The obturator is then withdrawn from the conduit leaving the conduit in place. A flexible collar is wrapped around the protruding end of the conduit and adhesively affixed to the skin to stabilize the conduit and maintain its position. A light-probe is then passed down inside the conduit to contact the vessel. The forked tip of the light probe engages the surface of the vessel to transmit pulsations from said vessel in a manner that will permit the operator to feel that the probe is properly centered on the vessel. A longitudinal groove running the entire length of the upper surface of the probe to its tip allows a needle to be advanced to the anterior wall of the artery to enter the lumen. With the needle properly positioned within the arterial lumen, a guidewire is inserted via the needle into the lumen, after which the needle and probe are removed leaving the guidewire in place. The conduit can remain in place for the entire procedure to maintain a tissue-free channel, or can be removed over the guidewire.

Accordingly, it is an object of the present invention to provide a group of coacting tools, some capable of independent action, which facilitate percutaneous vascular entry by efficiently enabling accurate percutaneous puncture of blood vessels.

It is another object of the present invention to eliminate double-wall punctures of vessels, to more accurately locate and position the needle for puncturing a vessel, to enable visualization of a vessel prior to puncturing the vessel in order to reduce the number of attempts necessary to successfully puncture a vessel.

It is another object of the present invention to minimize trauma and tearing of the blood vessel during puncture.

It is another object of the present invention to avoid mispositioned punctures in the side of a vessel.

It is another object of the present invention to provide a dissecting-retracting tool having handles which are both angled and offset for increased comfort during squeezing action, due to the designed range of motion from opened to closed position.

It is another object of the present invention to provide a dissector-retractor for vascular puncture having laterally offset handles positioned to the side of the device, out of the direct line of sight, in order to provide unobstructed viewing of dissection.

It is another object of the present invention to provide a dissecting-retracting tool that spreads tissue as handles are squeezed and are moved to a closed position.

It is another object of the present invention to provide a dissector-retractor having a spread power grip which provides maximum squeezing force by allowing the handles to remain in a slightly open position (i.e., full dissection) when the instrument fingers are in the fully open position and thus, the range of separation of the tips is within the range of maximum strength for the gripping/squeezing action of the hand.

It is another object of the present invention to provide a dissector-retractor having angled fingers for unobstructed viewing of dissection. The instrument fingers are at a 20 degree to 80 degree angle to the plane of the dissector handles, moving them out of the plane of the handles and the hand of the operator, and can be located on a plane above or below the level of the handles.

It is another object of this invention to provide a dissector-retractor having dissecting fingers capable of spreading underlying tissue to create a broad, clear channel down to the blood vessel.

It is another object of the present invention to provide a dissector-retractor having tapered fingers with tapered cylindrical passages formed in the fingers to create a cylindrical channel down to the blood vessel when the fingers are in the fully open position.

It is still another object of the present invention to provide a dissector-retractor whose dissecting fingers at the tips taper to a point to allow for easier dissection in both the downward and forward direction. Further, the bottom-to-top angle of the ends of the fingers match the angle of entry, and the side-to-center angle on the lateral surfaces of the fingers facilitates blunt dissection used in the fingers.

It is still another object of the present invention to provide a dissector-retractor having three-point stabilization of the apparatus when articulating the fingers by means of the index finger in an advanced foremost position, the thumb in a rear position, and the remaining fingers in another rearward position. This allows the index finger to apply downward pressure on the tips during dissection, and accurately control the direction of entry, thereby gaining greater control in manipulating the instrument.

It is another object of the present invention to provide a dissector-retractor having a contoured finger cup thereby allowing the index finger to apply forward and downward pressure on the tips during dissection, as well as overall stabilization of the instrument.

It is another object of the present invention to provide a dissector-retractor having a contoured finger rest for the index finger when not located in the actuating position.

It is another object of the present invention to provide a dissector-retractor having depth markings on the dissecting fingers which indicate the depth of the dissection, and hence the selection of lengths and types of coacting apparatus in accordance with the depth shown on the markings.

It is another object of the present invention to provide a dissector retractor having a locking mechanism that holds the dissecting tips open to a specific position.

It is another object of the present invention to provide a dissector-retractor which allows for a clear path of sight through the spread dissecting fingers to the very tips of the dissecting fingers.

It is another object of the present invention to provide a dissector retractor having spread instrument handles which allows for operation over the strongest range of thumb-to-finger and/or hand position, thus allowing the greatest force with the least exertion.

It is another object of the present invention to provide access-conduit for use with a dissector-retractor, which creates an open channel from the skin surface down to the blood vessel and coacts with a channel formed by the blunt dissecting fingers.

It is another object of the present invention to provide an access-conduit having a central longitudinal groove to guide an illuminated light probe or needle down the center of the tube to the center of a blood vessel. Further, this groove is also used to orient the access-conduit when coacting with the obturator.

It is another object of the present invention to provide an access-conduit having an angled and curved distal tip, a top-to-bottom angle to match the angle of entry and a side-to-side curve to match the curve of the blood vessel, to capture a blood vessel and center the tube over the blood vessel.

It is another object of the present invention to provide an access-conduit adapted for use with a dissector-retractor which can be made in several lengths to match the appropriate skin-to-vessel distance necessary to contact the blood vessel involved.

It is still another object of the present invention to provide an access-conduit made from material which is light-transmitting to convey light through the walls of the tube to the vessel and/or to be made from an opaque material with an opaque surface to reflect light directed down the access-conduit towards the blood vessel.

It is still another object of the present invention to provide an illumination probe to illuminate the channel down to the blood vessel as well as to be used for locating the vessel by feeling for the pulse with the tip of the probe or to explore the vessel to determine if the vessel is unsound.

It is still another object of the present invention to provide an illumination probe having an angle curved distal tip to fit over the blood vessel and feel the pulsations of the vessel, the distal tip having a top to bottom angle to match the angle of entry of the probe and having a side to side curve to match the curve of the blood vessel.

It is still another object of the present invention to provide a needle guide probe having a longitudinal channel that acts as a guide for a needle down the centerline of the probe to the center of a blood vessel to allow for a central puncture It is still another object of the present invention to provide a needle guide probe having a grooved channel which acts as a guide for a needle down the center of the guide to the center of the blood vessel to allow for a central puncture.

It is still another object of the present invention to enable coaction of positioning between the-access-conduit and the needle guide probe, and the needle guide probe with the access-conduit.

It is still another object of the present invention to provide for an illumination probe made of a material which can be illuminated, and which transmits light through the body of the illuminating probe to its distal end to illuminate the operative site.

It is still another object of the present invention to provide for an illumination probe which can be made from opaque material with an opaque surface to reflect light directed down the conduit towards the vessel to be punctured.

It is still another object of the present invention to provide an obturator which can hold one or two conduits, with each conduit on an opposite end with the conduits being of dissimilar size and/or shape.

It is still another object of the present invention to provide an obturator which is constructed to properly insert a conduit in an appropriate orientation with respect to the vessel to be punctured.

It is another object of the invention to provide an obturator with opposite ends rotated 180.degree. in relation to each other so that the angle at the distal tip at one end is parallel to the angle at the distal tip of the other end, thus providing an end surface that is parallel to the skin to assist in proper visual orientation of the conduit/obturator assembly.

It is still another object of the present invention to provide an obturator having a mid-section configured to allow for removal of the dissector-retractor from a coacting conduit/obturator assembly.

It is still another object of the present invention to provide an obturator that includes a retention mechanism to hold the conduit in position during manipulation of the conduit/obturator assembly.

It is still another object of the present invention to provide an obturator which is constructed to facilitate action by the operator to easily and accurately push the conduit and release same from the obturator.

It is still another object of the present invention to provide an obturator which is constructed with a partial shoulder to act as a stop for the access-conduit as it is being placed and held on the obturator, and to allow for access to the end of the conduit.

It is another object of the present invention to provide an obturator having an angled and curved distal tip to capture the blood vessel, and hold the obturator in place. The distal tip is angled from top to bottom to match the angle of entry and is curved from side to side to match the curve of the blood vessel.

It is still another object of the present invention to provide an obturator which is constructed having a depression to allow for access to the end of the conduit.

It is another object of the present invention to provide a method for puncturing a blood vessel which provides for coaction between a dissecting retracting tool, a conduit mounted on an obturator and a needle guide path in appropriate sequence to enable clear visualization of the channel from the skin incision to the blood vessel to be punctured and/or accurate positioning of the puncture in the vessel.

It is another object of the present invention to provide a method which allows for capture of the blood vessel by the distal end of the conduit and obturator.

It is another object of the present invention to provide a method which allows for capture of the blood vessel by the needle-guide probe.

It is another object of the present invention to provide a method which allows palpation of the blood vessel by transmission of the pulse along a needle-guide probe from the blood vessel to the operator.

It is another object of the present invention to provide a method which allows palpation of the blood vessel by transmission of the pulse along an obturator from the blood vessel to the operator.

It is another object of the present invention to provide a method which allows palpation of the blood vessel by transmission of the pulse along the dissector-retractor from the blood vessel to the operator.

It is another object of the present invention to provide apparatus to enable application of specific localized pressure to the site of a percutaneous entry of a blood vessel.

It is another object of the present invention to provide apparatus for reducing the bleeding at the entry site of a vessel by direct application of a sponge to the site of the vessel opening.

BRIEF DESCRIPTION OF THE DRAWINGS

For a more complete understanding of the present invention, reference may be had to the following description of exemplary embodiments of the present invention considered in connection with the accompanying drawings, in which:

FIG. 6 is an enlarged view of the tips of the fingers of the blunt dissecting tool shown in FIG. 1;

FIG. 8 shows an enlarged view of the end of the conduit shown in FIG. 11 from the front;

FIG. 11 is an enlarged view of the conduit;

DETAILED DESCRIPTION OF THE PREFERRED EMBODIMENTS

Figure 1:
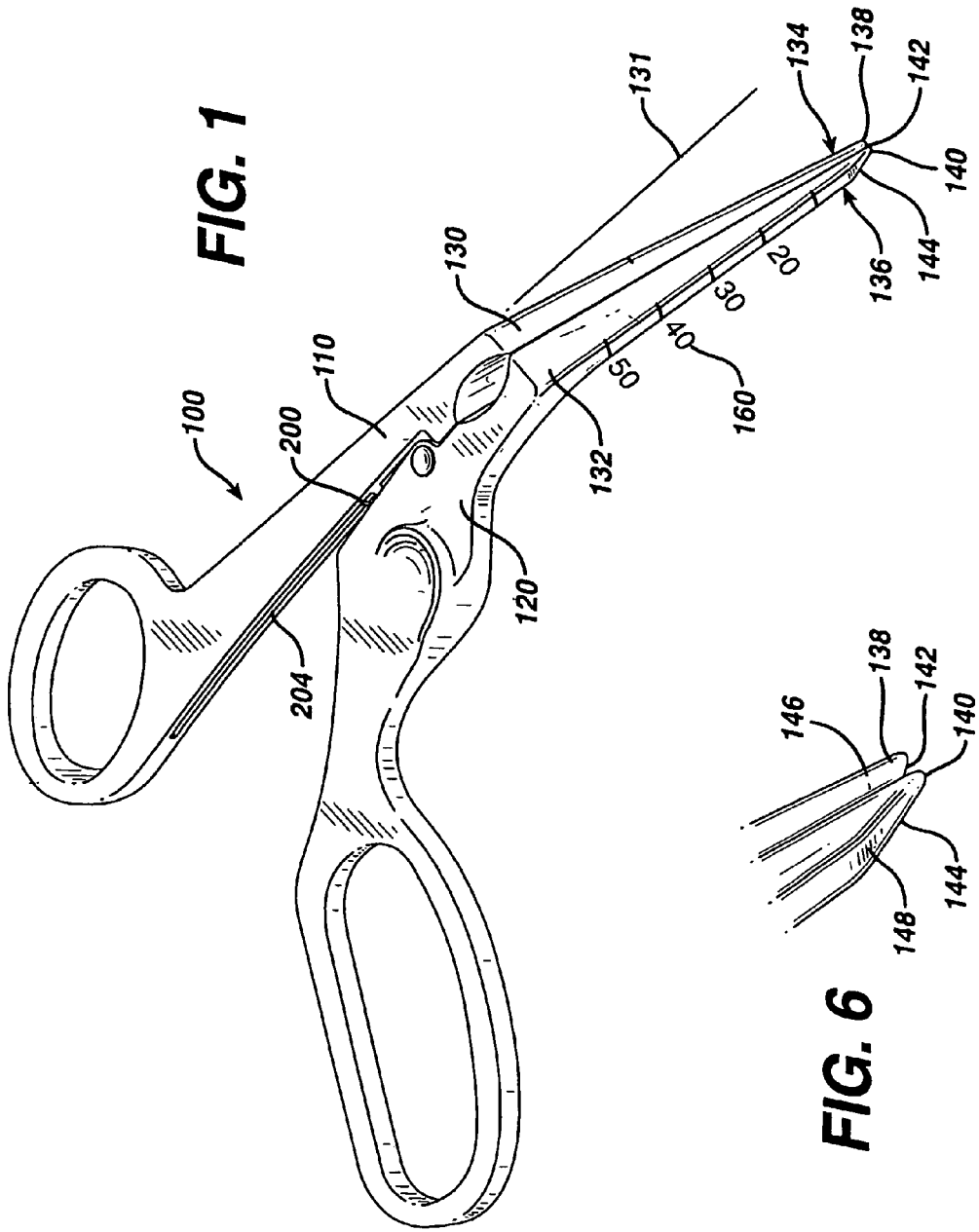
FIG. 1 is a perspective view showing the blunt dissecting tool of the present invention in the closed position.

As shown in FIG. 1, a dissector/retractor tool is generally indicated at 100 and has 2 arms generally indicated at 110 and 120. The arms end in fingers 130 and 132 which are bent from the plane of the arms at an angle 131 of anywhere from 20 degrees to 80 degrees but preferably from 30 degrees to 45 degrees. The ends of the fingers 134 and 136, respectively on fingers 130 and 132 have points 138 and 140 which are pointed but not sharp and not rounded. The points are chamfered at the bottoms 142 and 144, respectively. The chamfer provides an angle which is supplementary to the angle of the fingers to provide a flat plane with the horizontal. Chines on the flat plane at the outside lower leading surface of the fingertips 146 and 148, respectively provide for a sharp bottom when the dissecting fingers are acting together.

Figure 2:
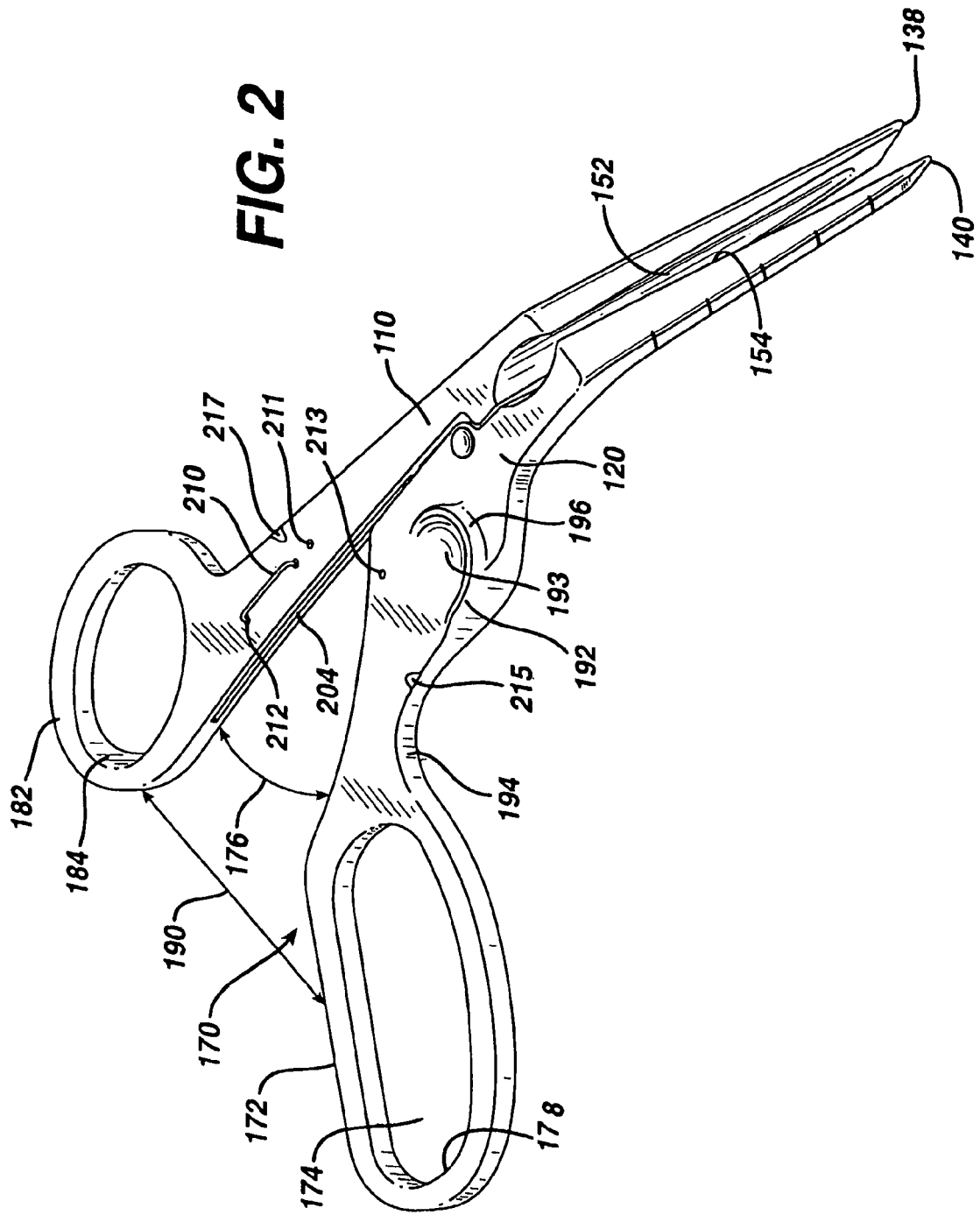
FIG. 2 is a view of the blunt dissecting tool shown in FIG. 1 with the dissecting fingers in the open position.
Figure 3:
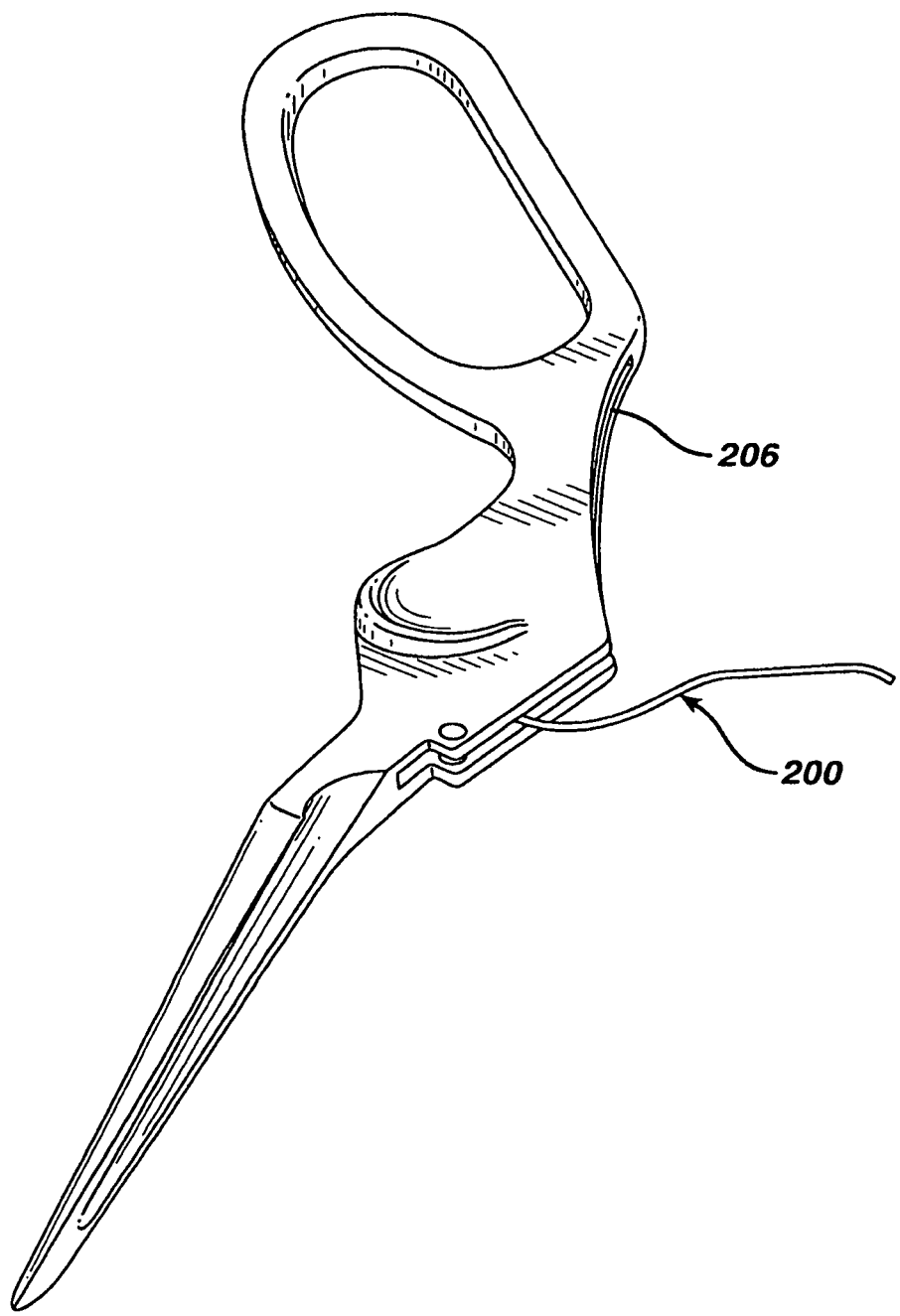
FIG. 3 is a view of the arm having the finger grips of the blunt dissecting tool shown in FIG. 1.

As shown in FIG. 2, moving the arms of the dissector-retractor together will spread the fingers. The fingers of the dissector-retractor, as shown in FIGS. 2 and 3, have tapered cylindrical passages formed on the facing surfaces so that when the fingers are spread to the maximum position, a cylindrical path is formed from the top of the arms to the tips of the fingers. The tapered cylindrical passages are indicated at 152 and 154 on the inner surfaces of thumb and finger arm 110 and 120, respectively. This cylindrical passage will allow a clear line of sight from the base of the fingers down to the tips 138, 140.

As seen in, FIG. 1, depth marking indicia 160, herein enumerated in mm., are formed on the top surface of the fingers and are oriented for viewing from the finger-grip portion. These indicia are an indication of the depth of tissue that has been penetrated by the fingers of the dissector-retractor. This provides an indication to the operator as to the length of conduit that will be necessary for the next step in the procedure.

The handle portion of the dissector-retractor, generally indicated at 170, contains a finger grip 172 possessing an oblong opening for two, three or four fingers. The finger grip is at an angle 176 to the thumb grip to provide the most comfortable position of the partially closed hand while holding the device.

Additionally, the offset of the finger grip provides for clear-unobstructed view over the arms, especially dissecting fingers of the dissector-retractor. There is a chamfer 178 on the inner surface of the finger grip to provide a smooth radius for comfort of the hand. The thumb grip 182 has a chamfer 184 on the inside of the grip. There is a space 190 between the finger grip and the thumb grip when the dissecting fingers of the arms are in the maximum open position. This space or distance provides a position in which the fingers and the thumb are separated for the maximum strength of grip for the human hand.

The chamfered slopes on the sides of the hand grips, 178 for the fingers and 184 for the thumb, provide for maximum comfort. There is a also a forefinger stabilizing function generally indicated at 192.

The forefinger-stabilizer includes a resting position 194 for the forefinger when this finger is not being used for any special purpose, and a forefinger well or cup 193 which has a forward wall 196. The purpose of the forefinger well is to allow a position where the forefinger can be placed to exert force without slipping in controlling the dissector-retractor without slipping. The front wall 196 allows the forefinger to press downward and forward on the dissector-retractor. Together, the forefinger-well 193, the thumb 182, and the finger grip 172, establish a three-point stabilized position for holding and controlling the dissector-retractor during use.

Note that the forefinger-well 193 is displaced to the side of the dissecting fingers to maintain a clear line of sight to the cylindrical passage formed in the dissecting fingers when they are spread.

As shown in FIGS. 2 and 3, a spring mechanism generally indicated at 200, as shown on FIG. 2 or 3, having a spring with recessed channels 204,206 for the spring is provided to cause the fingers of the dissector retractor to rest normally in the closed position with the hand grips in the most widely spread position.

A locking bar 210 is mounted in a storage position on the thumb arm, there being two detents 212 or bore holes to hold the ends of the locking bar 210 in a passive non-utilized position. When it is desired to maintain the dissecting fingers in a spread position, the locking bar 210 can be placed in bore holes 211 and 213 on the arms 110 and 120, respectively, to hold the arms apart in the spread position against the action of the spring. Alternatively, a locking bar can be used to engage cut-outs 215,217 on the sides of the arms to hold the position with dissecting fingers.

Figure 4:
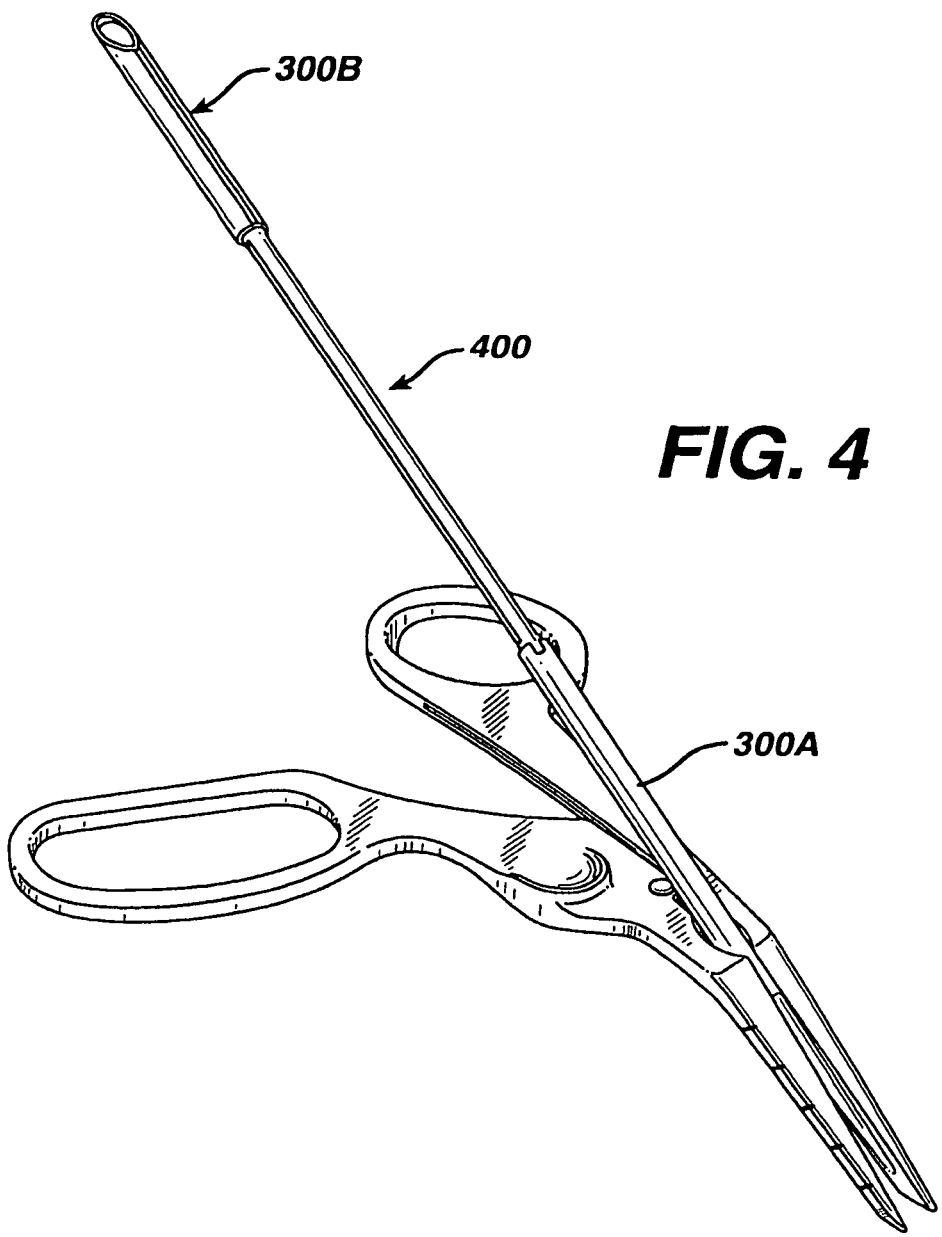
FIG. 4 is a view of the blunt dissecting tool of FIG. 1 together with coacting conduit and obturator.

As shown in FIG. 4, two conduits 300A,B are mounted on an obturator generally indicated at 400. The conduits on the obturator fit within the cylindrical passage formed in the spread fingers of the dissector-retractor. Note that conduit 300A is longer than conduit 300B, as was previously discussed in connection with the markings 160 on the top face of the dissecting fingers. The diameters of the obturator ends and associated conduits can also vary.

Figure 5:
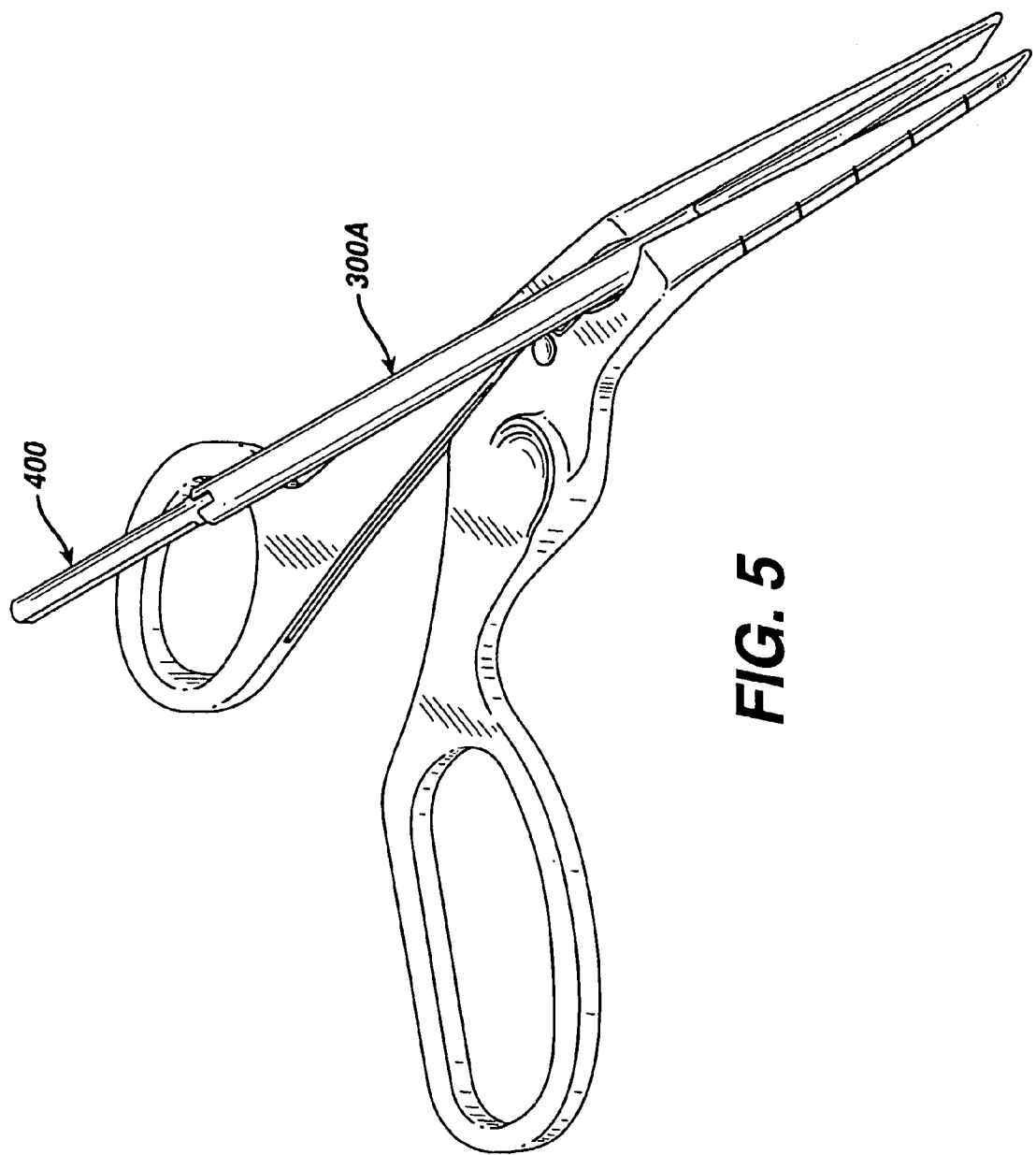
FIG. 5 is an enlarged view of FIG. 4.

FIG. 5 is an enlarged view showing the lower conduit on the obturator within the cylindrical passage.

Figure 7:
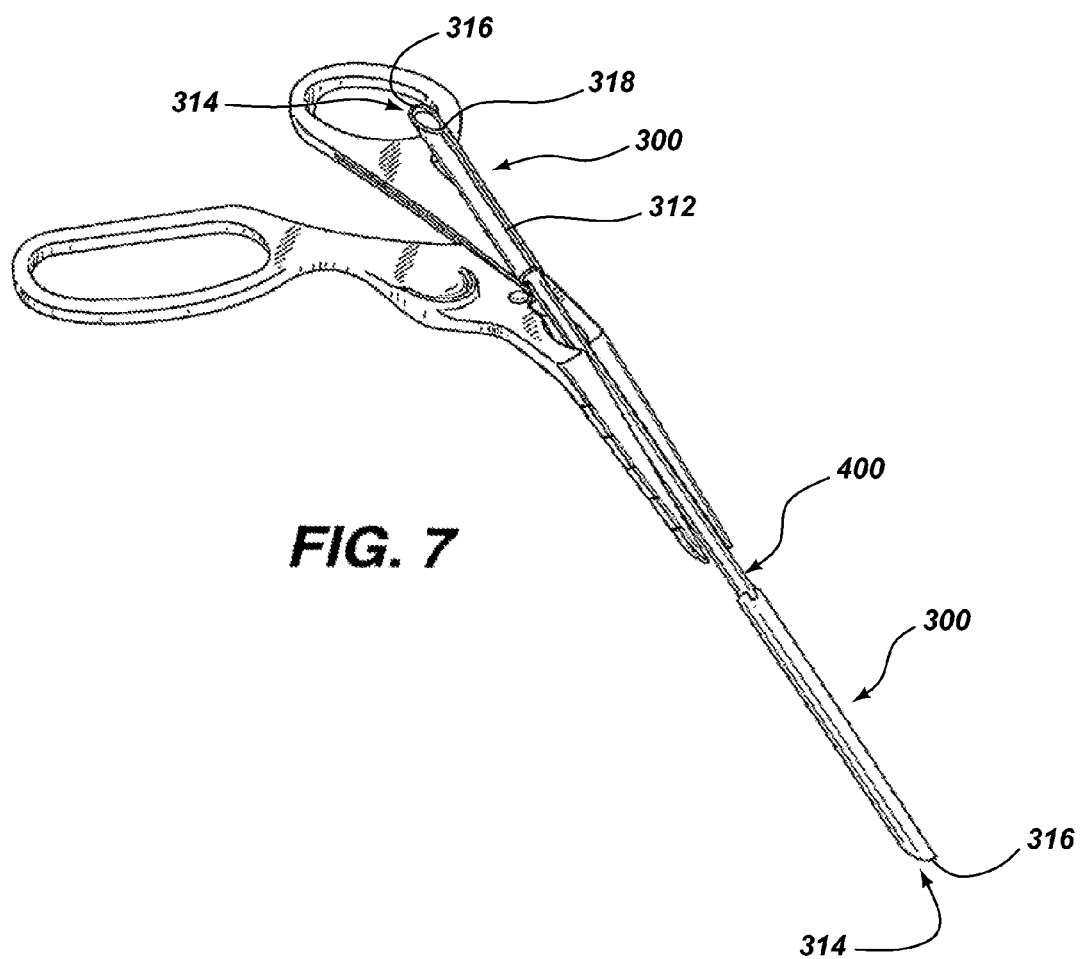
FIG. 7 is a view similar to FIG. 4 with the blunt dissecting tool removed up along the obturator in a position for separation from the obturator and conduit assembly.

In FIG. 7, conduit 300 is shown assembled onto obturator 400, with one conduit mounted on each end of the obturator. Conduit 300 has a longitudinal guide groove 312 extending to the conduit's distal end 314, the end inserted into the patient, and the guide groove is open to the distal end. This distal end is angled from 20-80 degrees to the longitudinal axis of the conduit, and this angle is matched to the angle of the instrument fingers to the instrument arms. The angle at the distal end forms forward tip 316 at the distal portion of the angled distal end and rearmost point 318 located at the proximal portion of the angled distal end. Guide groove 312 intersects with the angled distal end at rearmost point 318 of the angled end. In the embodiment as shown in FIG. 8, the longitudinal guide groove 312 may be formed as a longitudinal protuberance 310 protruding from the outer surface of conduit 300.

As shown in FIGS. 8 and 11, once the conduit is moved or advanced down to the bottom of the dissecting fingers, and is positioned over the blood vessel to be punctured, the matching curvatures at the bottom of the obturator and the bottom of the conduit respectively, will help the conduit find or position itself on top of the vessel. See FIGS. 8 and 11 for enlarged views of the conduit and FIG. 12 for an enlarged view of the obturator.

In FIG. 11, the conduit generally indicated at 300 has an end contour or profile adapted to coact with the surface of the blood vessel. The diameter of the conduit generally indicated at 302 extends for a length 304, which coincides with the length of the wide end of the obturator to maintain the conduit fully on the obturator while it is being inserted through the cylindrical passage of the dissecting fingers. The conduit creates an open access channel from the skin surface down to the blood vessel. The tip is scooped out at 308 so as to have a left to right curvature that will conform to the surface of the blood vessel and continue to engage the vessel even if the conduit is raised to a greater angle than its intended angle of entry.

Additionally, a guide channel 312 in the conduit acts to align itself and receive a guide rib 420 on the obturator to align the conduit with the obturator, as will be discussed further below.

The angle at the bottom of the conduit is the same angle as the bottom of the dissecting fingers and will be the same as the bottom of the obturator which is supplementary to the angle of the dissecting finger so as to provide a generally horizontal flat surface to lie fully in contact with the vessel to be punctured.

Figure 12:
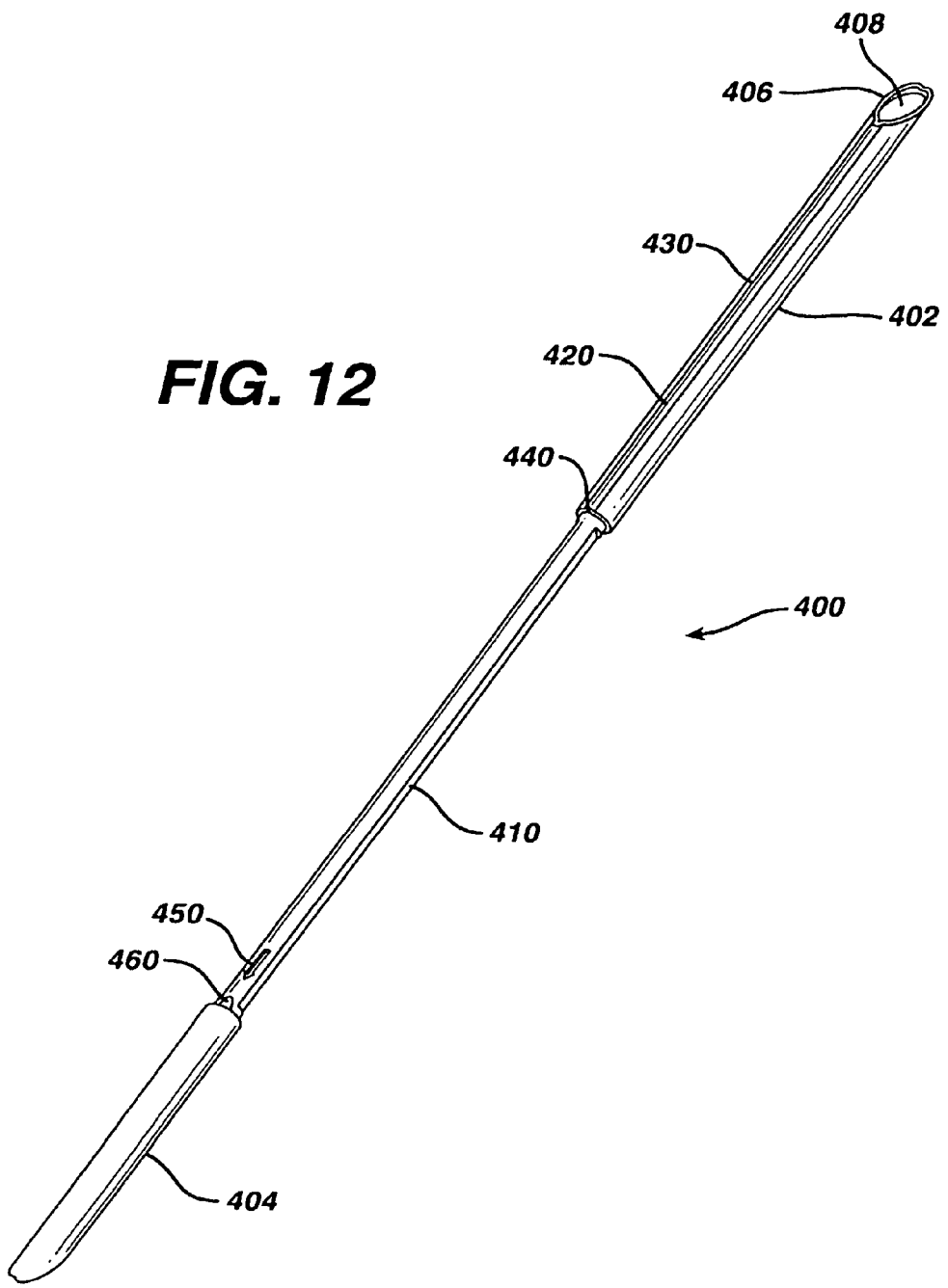
FIG. 12 is an enlarged view of the obturator.
Figure 14:
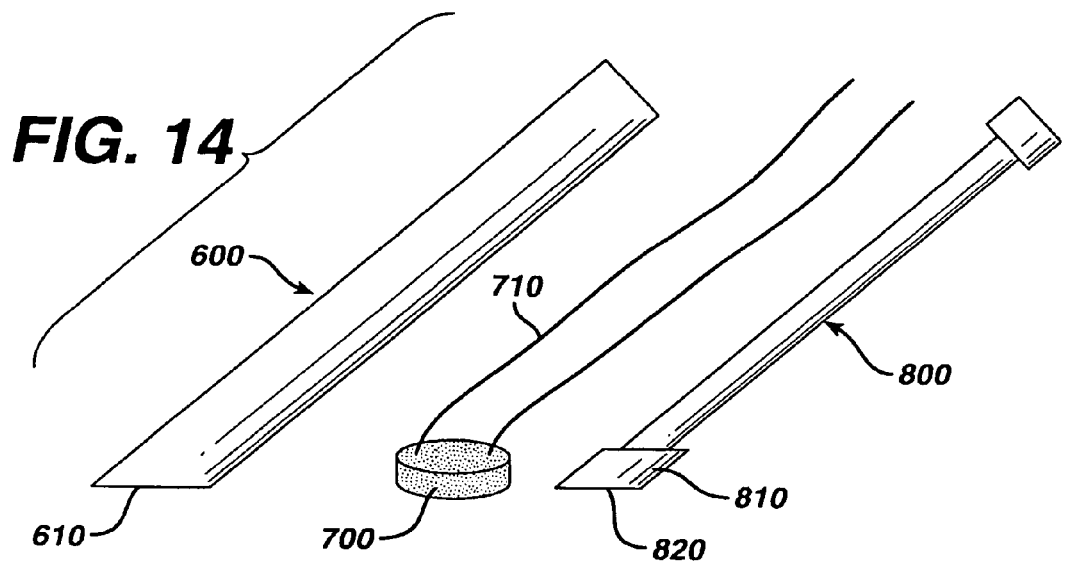
FIG. 14 is a view showing the elements used for reducing the bleeding from a percutaneous entry to a vessel.
Figure 15:
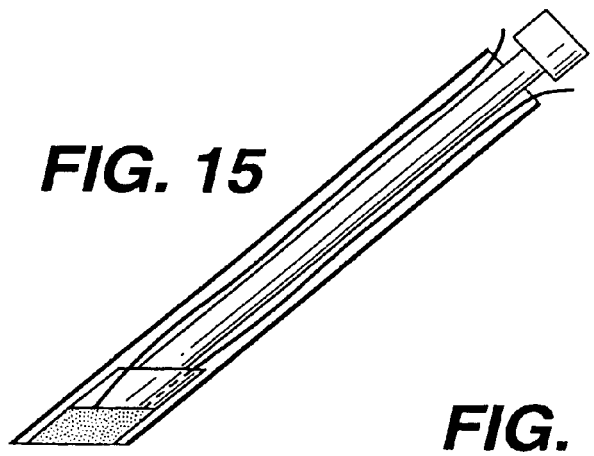
FIG. 15 shows the elements of FIG. 14 in the working relationship.

As shown in FIG. 12, the obturator generally indicated at 400 has a long end 402 and a shorter end 404. We will describe only the longer end for purposes of brevity. The longer end has an end 406 possessing a profile similar to that of the conduit in that it has a chamfer angle supplementary to the angle of the dissecting fingers and equal to that of the conduit, and is also curved from side to side to facilitate contact with the rounded surface of the vessel to be punctured. The opposite end 407 has a profile similar to end 406 but rotated 180 degrees to provide an end surface parallel to the opposite end surface. The parallel opposing end surfaces aid in visual orientation of the obturator/conduit assembly in the dissector-retractor tool.

The obturator has a guide rib 420 running the length of the larger diameter section 402 and which is adapted to coact with a guide groove 312 in the conduit to position the conduit and prevent rotation of the conduit. A tab 430 formed in the larger section of the obturator provides a spring friction contact with the conduit to prevent movement of the conduit with respect to the obturator.

A stopping shoulder 440 is provided at the end of the wide section of the obturator to prevent the conduit from backing up onto the obturator. Additionally, an arrow pointer shown as 450 on the smaller end of the obturator but which also appears on the other end, provides a tactile contact to give the operator an indication of the orientation of the obturator and conduit assembly. A depression 460 in the obturator allows the finger access to the end of the conduit when pushing conduit off the obturator.

As shown in FIG. 5, the conduit/obturator assembly is placed within the tubular channel created by the spread fingers of the dissector-retractor. Subsequently, the dissector-retractor is withdrawn by sliding the dissector-retractor up the conduit as shown in FIG. 7 until it reaches the narrow central section of the obturator 410, at which point the obturator will fit loosely in the cylindrical channel created by coaction of the cylindrical channel formed in the dissecting fingers, and this will facilitate removal of the obturator from the dissector-retractor. The obturator is then removed from the conduit leaving the conduit in place.

Figure 13:
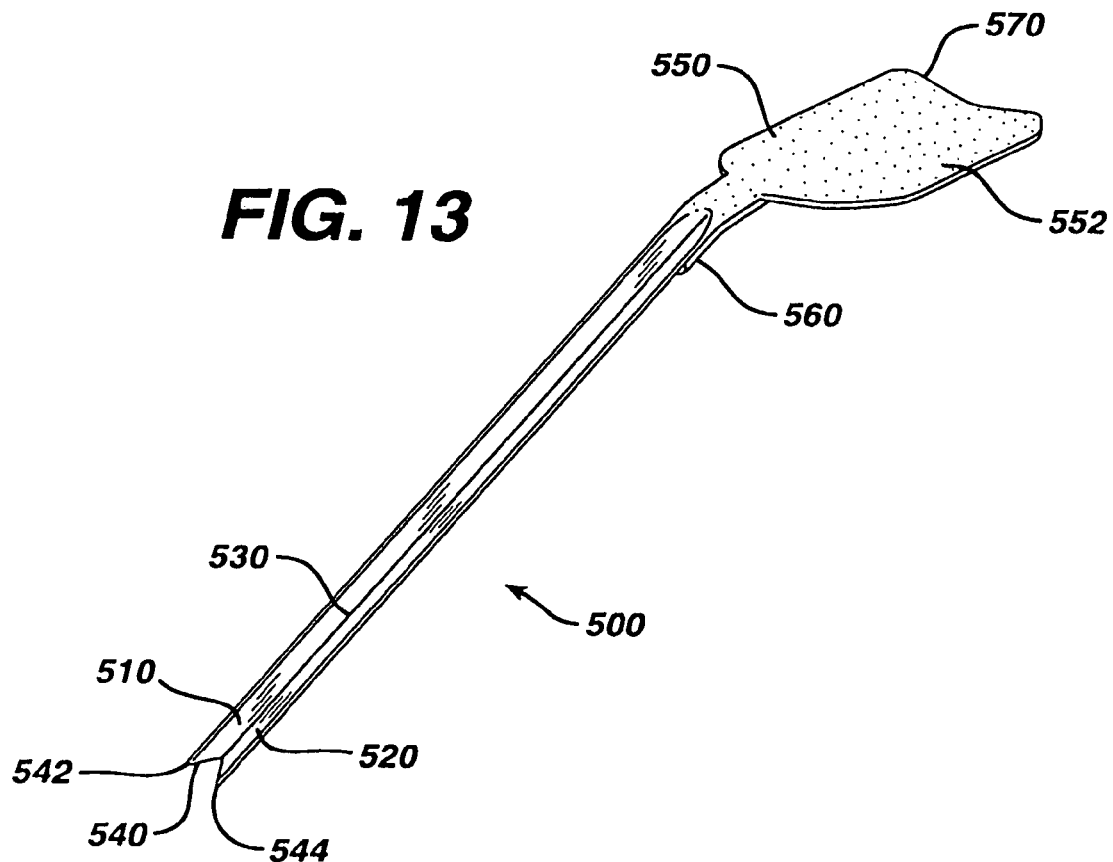
FIG. 13 is an enlarged view of the needle guide.
Figure 9:
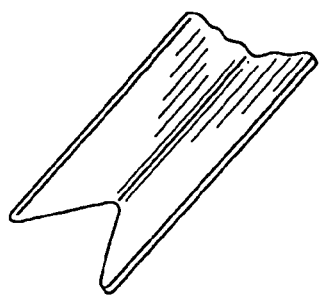
FIG. 9 is an enlarged view of the end of the needle guide shown in FIG. 13.
Figure 10:
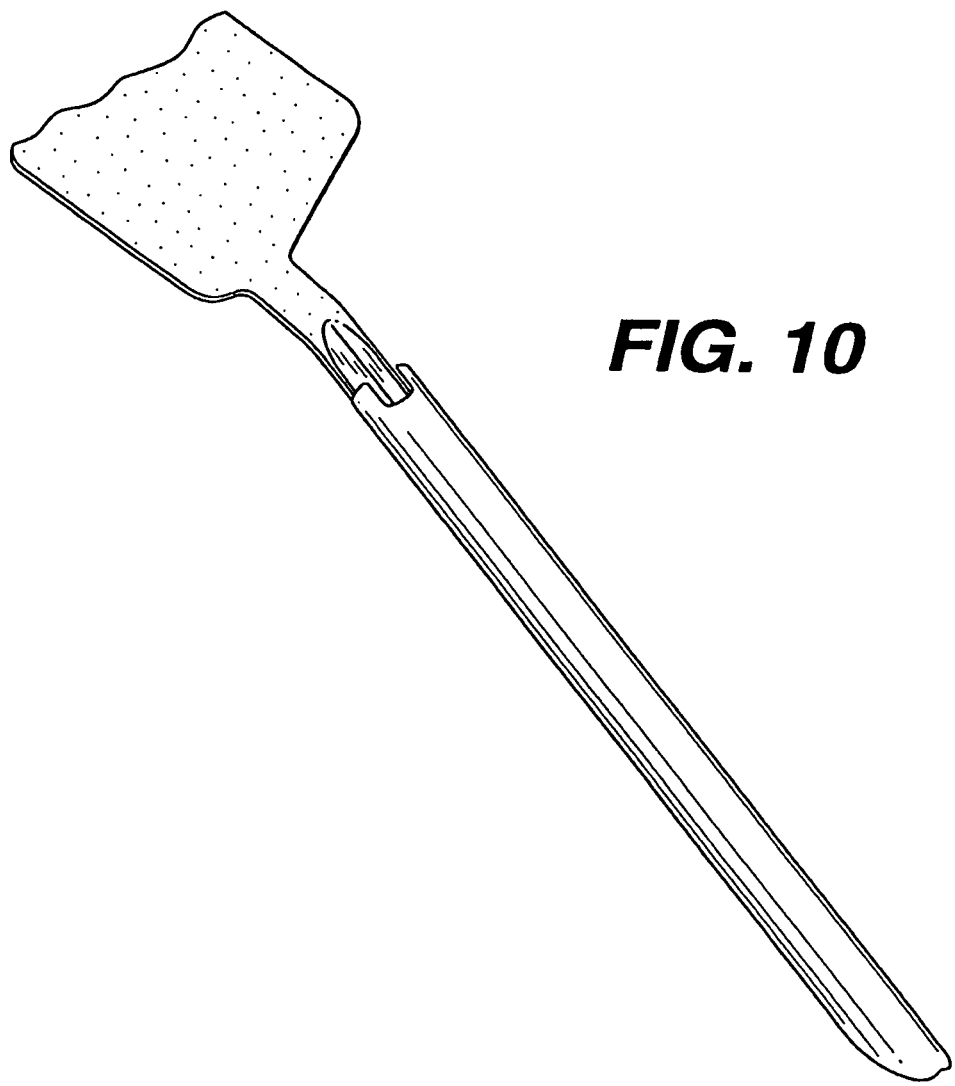
FIG. 10 is a view showing the needle guide within the conduit.

As shown in FIGS. 9, 10 and 13, a needle guide-illuminator is provided which is adapted to fit within the conduit once the obturator has been removed.

As shown in FIG. 13, the needle guide-illuminator is generally indicated at 500 and has two panels or wings 510,520 which form a trough or groove 530 to guide a needle from the handle portion 550 down to the end of the guide 540. The end of the guide 540 has two tips 542 and 544 which are formed by the end of the guide and which have a scooped out portion so that the ends of the guide 542,544 will overlie and capture between them an underlying blood vessel or body structure.

Additionally, the panels 510,520 form a concavity upward. When fitted within the conduit as shown in FIG. 10, the needle-guide illuminator has a stop member 560, which will position the needle guide so that the end 540 is in registration with the end of the conduit 306, and a rib guide 580 on its underside to align it properly within the conduit. There is an attaching point 570 on the handle of the needle guide illuminator for attachment of a fiberoptic bundle. Also there is a roughened or beaded finger grip 552, offset from the guide path 530 on the handle 550, for manipulation of the light guide.

Because of the longitudinal play between the needle guide and the conduit, the needle guide will be capable of movement with a pulsating vessel, such as the femoral artery, and this will be transmitted to the operator who is gripping the handle. He will then be able to manipulate the needle guide to position it on the blood vessel to be punctured and will be able to see down to the point of the puncture through the conduit.

The conduit and the needle guide can be made of optically clear material so that a fiberoptic bundle when attached to the end of the needle guide will provide a stream of light within the conduit that will illuminate the operative site of the puncture.

Additionally, the conduit and the needle guide can have an inner reflective surface that will help reflect light within the conduit to further enhance the illumination of the puncture cite.

The method of use can now be discussed. The operator begins by palpating the femoral artery. The line of maximal pulsation is ascertained, a skin-to-artery trajectory is pictured, and a small incision in the skin is made with a blade. The dissector-retractor is now employed to create a skin-to-vessel channel. The point of the tips of the dissecting fingers are inserted through the skin incision at a desired angle (usually between 30 degrees and 45 degrees) and advanced by forward pressure directed by forefinger, alternating with squeezing of the handles to open the dissecting fingers, thereby performing a blunt dissection until the femoral artery is reached.

The under-surface of the tips is configured to be parallel to the artery so that upon reaching this vessel, the closed tips can rest upon and contact the artery and transmit arterial pulsations. At this point the dissecting fingers are opened, the channel can be illuminated and the artery inspected visually, if desired.

Having ascertained by palpation and/or visualization that the subcutaneous channel has reached the femoral artery, the tubular access conduit is inserted (with the use of the obturator) between the dissectors fingers down to the arterial surface. The configuration of the conduit's distal end, angled to parallel the artery and concave left-to-right to match the radial curvature of the vessel, permits the coacting distal ends of the conduit and obturator to engage the arterial surface and capture it in precise alignment. Slight downward pressure permits appreciation of the arterial pulsation and verification that the conduit is centered in the artery. The dissector/retractor is now removed over the obturator leaving the obturator with the conduit in place.

The obturator is then withdrawn from the conduit and the obturator is set aside. A flexible collar is wrapped around the protruding proximal end of the conduit and the adhesive-bearing wings pressed against the skin, thereby stabilizing the position of the conduit. The channel provided by the conduit is ample for irrigation and suction, if and when needed, to enhance visualization of the vessel and its pulsations. Additional light may be introduced into the conduit by an external focused lamp, such as those designed to be worn on the forehead, or the illumination may be provided by attaching a fiberoptic source to its proximal end.

The illumination probe is then passed down the conduit along its bottom surface where it is guided by a thin channel in the conduit. When the contoured tip of the illumination From the above discussion one can appreciate the value of vascular puncture under direct palpation and/or observation, where the artery is clearly visualized, its pulsation is clearly seen and topical. Also the artery is distinguishable from the adjacent femoral vein and nerve, which can be damaged by offline passage of the needle. The PERCUTANEOUS ENTRY SYSTEM of the present invention provides a new and superior method for the percutaneous introduction of catheters and other medical instruments into the vascular system under direct palpation and/or vision. The unique features of the system enable a truly central puncture of the blood vessel at the desired angle of entry, thereby minimizing trauma to the vascular wall and adjacent structures.

FIGS. 14, 15, 16, and 17 show apparatus for a closure pressure sponge assembly to be used with the blunt dissecting apparatus for percutaneous entry through blood systems.

Since percutaneous entry into a blood vessel requires a puncture of the blood vessel, it may result in an irregular puncture. The puncture must eventually be closed for hemostatis. The traditional method has been to apply gross pressure to the area of the puncture. The process is not localized because force is applied to a broad area of skin. Complications, particularly hematoma of various sizes, are common.

To reduce this problem, the present invention provides an add-on kit for the percutaneous dissecting and access system which includes a tubular conduit generally indicated at 600 which provides a clear cylindrical path from the skin of the patient to the vessel that has been entered. Thus direct pressure that is specific and localized to the entry site is possible. An obturator or sponge pusher generally indicated at 800 is also included. The sponge pusher or obturator is intended to exert pressure directly and exclusively at the site of the entry into the vessel to maintain pressure for a length of time needed for clotting and hemostatis of the vessel puncture site.

Lastly, a "sponge" generally indicate at 700 which may be of a non-woven structure, or a woven gauze-like mesh design, and may also be of a bioresorbable material, is intended to be inserted into the conduit. The sponge pusher would follow behind tie sponge to deliver the sponge to the site of the entry and exert a resilient force at the desired site. The sponge pusher would maintain light pressure on the sponge and hence on the vessel that has been entered until natural hemostatis occurs.

Upon accomplishing hemostatis, the bioresorbable sponge may be removed or could be left in place. To facilitate removal of the sponge it may be necessary to stitch the sponge with a long suture generally indicated at 710 prior to its insertion into the conduit. In this way, the operator can remove the sponge simply by tugging on the suture.

It should be noted that bottom of the conduit is similar to the bottom of the conduit previously described. The distal end 610 is cut at an angle which would enable the distal end to lie flat at the angle of percutaneous entry.

Additionally, the cut of the angle through the cylindrical conduit produces an oval shape having a long axis intended to lie parallel to the vessel being entered and the bottom also has a curved surface perpendicular to the long axis 620 of the oval formed at the bottom. The curve 630 enables the conduit to lie relatively flat on the vessel to be entered or which has been entered.

The very tip of the conduit 640 is also opened up to enable the conduit to lie and find the vessel that it is to coact with.

The pusher could be similar to the obturator previously discussed. The necessary elements of the pusher are a distal end 810 having a bottom surface 820 similar to the bottom surface of the obturator previously described and adapted to form the same angle as the distal end of the conduit and have a shape complementary to that of the distal end of the conduit to form a continuous surface with the end of the conduit so that a uniform pressure can be applied to the sponge so as to have the sponge seek around or curve with the surface of the vessel that has been entered.

Figure 16:
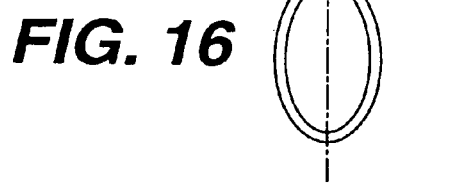
FIG. 16 shows the bottom of the conduit shown in FIG. 14.
Figure 17:
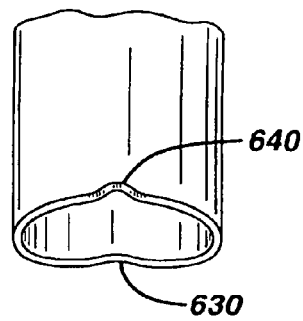
FIG. 17 shows the bottom of the conduit from the front elevation.

Therefore, the bottom of the pusher will be oval in shape similar to that shown in FIG. 16 having a long axis and a short axis with a curved portion perpendicular to the long axis to allow it to rest with a greater surface area on, the vessel to be entered. This shape will then push the sponge into greater conformity with the surface of the vessel. The length of the pusher must be sufficient so that an end of the pusher will extend from the end of the conduit when the sponge has been pushed down to the bottom of the conduit and is resting on the vessel.

The advantage of direct visualization may be even more valuable for venous entry, since pronounced pulsations to define the vessel are absent and venous walls are thinner, hence more easily damaged. Also venous entry (for example into the jugular or subclavian) relies heavily on superficial anatomic landmarks which are less reliable than direct visualization.

Some advantages of the present invention over prior art are that the dissection tool has angled dissecting fingers to allow for unobstructed view of the surgical site, that the handles are offset from the central axis of the tool thereby allowing for additional unobstructed view of the surgical site, that the range of motion of the handles are designed in such a manner so that maximum squeezing forces apply during dissection while opening the dissecting fingers, that the dissecting fingers of the instrument are concave in design through which surgical instruments can be passed to the vascular puncture site, that the fingers are broad to create a broad, clear channel, and that the access conduit contains a rounded distal end which hugs the blood vessel and orients the conduit into an optimal access position, that the access conduit contains a grooved bottom edge to guide the puncturing instrument into an optimal central position on the vascular wall and can be illuminated to provide better illumination, that the needle guide/illumination probe has a forked tip to engage the artery and hold it during puncture, and that the illumination probe contains a groove channel to guide the needle to a centrally located point on the vascular wall.

While the invention has been described in its preferred embodiment, it is to be understood that the words which have been used are words of description rather than limitation and that changes may be made within the purview of the appended claim without departing from the true scope and spirit of the invention in its broader aspects.

It will be understood that the embodiments described herein are merely exemplary and that a person skilled in the art may make many variations and modifications without departing from the spirit and scope of the invention. All such modification and variations are intended to be included within the scope of the invention as disclosed herein.

What is claimed is:

1. A conduit for use in apparatus and methods for percutaneous access to blood vessels or other target organs in a human body comprising:
   an elongate hollow tubular structure sized to fit within a body cavity and to access a human body structure, said tubular structure being open at both ends and having a proximal end and a distal end and a wall enclosing an inner passageway, said distal end angled from 20 to 80 degrees relative to the straight longitudinal axis of said tubular structure to create an angled opening at said distal end, said angled distal end comprising a forward tip located at a distal portion of said angled distal end and a rearmost point located at a proximal portion of said angled distal end, said tubular structure being axially straight over its entire length and having a longitudinal groove formed into an inner surface of said wall extending to said rearmost point at said angled distal end, said longitudinal groove being straight over its entire length.

2. The conduit of claim 1 wherein said
   longitudinal groove extends along the entire length of said inner surface from said rearmost point of said angled distal end to said proximal end of said hollow tubular structure.

3. The conduit of claim 1 wherein said distal end has a contour configured to engage the surface of the blood vessel or other target organ.

4. The conduit of claim 3 wherein said contour has a concave shape that matches the radial curvature on the outer surface of said vessel or said organ.

5. The conduit of claim 3 wherein said angled distal end comprises a distal tip that is scooped out so as to conform to the surface of the blood vessel or target organ such that it will continue to engage said vessel or organ if said access conduit is tilted upward to a greater angle than its intended angle of entry.

6. The conduit of claim 1 wherein the cross-section of said longitudinal groove has a curvilinear shape.

7. The conduit of claim 1 wherein said longitudinal groove is sized to interface with a needle.

8. The conduit of claim 1 wherein said proximal end is adapted for attaching a light source.

9. A conduit for use in apparatus and methods for percutaneous access to blood vessels or other target organs in a human body comprising:
    an elongate hollow tubular structure sized to fit within a body cavity and to access a human body structure, said tubular structure being open at both ends and having a proximal end and a distal end and a wall enclosing an inner passageway, said tubular structure being axially straight over its entire length and comprising a longitudinal access channel of a first diameter and a longitudinal guide channel of a second diameter less than said first diameter, said guide channel being formed as a longitudinal groove into the inner surface of said wall and extending to said distal end, said longitudinal groove being straight over its entire length;
    wherein said distal end is angled from 20 to 80 degrees relative to the straight longitudinal axis of said tubular structure to create an angled opening at said distal end, said angled distal end comprising a forward tip located at a distal portion of said angled distal end and a rearmost point located at a proximal portion of said angled distal end, and said longitudinal groove extends to said rearmost point at said angled distal end.

10. The conduit of claim 9 wherein said distal end comprises a contour configured to engage the outer surface of said vessel or said organ.

11. The conduit of claim 9 wherein said distal end comprises a distal tip that is scooped out so as to conform to the surface of the blood vessel or target organ such that it will continue to engage said vessel or said organ if said access conduit is tilted upward to a greater angle than its intended angle of entry.

12. The conduit of claim 9 wherein the cross-section of said guide channel has a curvilinear shape.

13. The conduit of claim 9 wherein said guide channel is sized to interface with a needle.

14. The conduit of claim 9 wherein said proximal end is adapted for attaching a light source.

15. A kit for percutaneous access to blood vessels or other target organs in a human body-comprising:
    A spreading instrument having:
        a first instrument arm and a second instrument arm, each disposed in a first plane;
        a finger grip at a proximal end of said first instrument arm;
        a thumb grip at a proximal end of said second instrument arm;
        first and second instrument fingers extending distally from the distal ends of the first and second instrument arms respectively, each of said instrument fingers being axially straight over their entire length;
    wherein said first and second instrument arms are movably coupled to allow movement of the first and second instrument fingers relative to one another upon movement of the finger grip and thumb grip relative to each other; and
    An elongate hollow tubular structure sized to fit within a body cavity and to access a human body structure, said tubular structure being open at both ends having a wall enclosing an inner passageway, a proximal end, and a distal end angled from 20 to 80 degrees relative to the straight longitudinal axis of said tubular structure to create an angled opening at said distal end, said angled distal end comprising a forward tip located at a distal portion of said angled distal end and a rearmost point located at a proximal portion of said angled distal end said tubular structure being axially straight over its entire length and having a longitudinal groove formed into an inner surface of said wall extending to said rearmost point at said angled distal end, said longitudinal groove being straight over its entire length.

16. The kit of claim 15 wherein said longitudinal groove extends along the entire length of said inner surface to the proximal end of said angled opening of said hollow tubular structure.

17. The kit of claim 15 wherein said distal end has a contour configured to engage the surface of the blood vessel or other target organ.

18. The kit of claim 17 wherein said contour matches the outer surface of said vessel or said organ.

19. The kit of claim 17 wherein said distal end comprises a distal tip that is scooped out so as to conform to the surface of the blood vessel or target organ such that it will continue to engage said vessel or organ if said access conduit is tilted upward to a greater angle than its intended angle of entry.

20. The kit of claim 15 wherein said longitudinal groove is sized to interface with a needle.

21. The kit of claim 15 wherein said proximal end has an interface for attaching a light source.

22. The kit of claim 15 wherein said first instrument finger and said second instrument finger both have an inner surface defining a rounded groove, tapered lengthwise at a constant rate towards a distal end of said rounded groove; and
    wherein, upon spreading the instrument fingers, the rounded grooves on the inner surfaces of the instrument fingers coact to partially define, between the rounded grooves, a cylindrical passage adapted to receive a tubular structure; and
    wherein said conduit fits within the defined portion of said cylindrical passage.

23. The kit of claim 22 wherein said first and second instrument fingers are disposed in a second plane at a first angle of 20 to 80 degrees below said first plane; and
    wherein said angled opening is at an angle to said straight longitudinal axis of said tubular structure that is substantially equal to the angle of said second plane relative to said first plane.

24. The kit of claim 23 wherein each of the distal ends of the instrument fingers has a bottom surface disposed in a plane substantially parallel to the plane defined by the distal end of said conduit when said conduit is grasped by said rounded grooves of said instrument fingers.

25. The kit of claim 15 wherein at least one of the instrument fingers has an outer surface bearing an index of distance from the distal end of the instrument finger; and wherein said conduit has an overall length measured from its distal tip to its proximal end that is greater than the distance corresponding to said index.

26. The kit of claim 15 further comprising a needle for puncturing a blood vessel or target organ, said needle sized to fit within and be advanced along said longitudinal groove.

27. A kit for guiding an elongate instrument to a blood vessel or target organ in a human body comprising:
   A conduit comprising a straight elongate hollow tubular structure sized to fit within a body cavity and to access a human body structure, said tubular structure being open at both ends having a proximal end, and a distal end and a wall enclosing an inner passageway, said distal end angled from 20 to 80 degrees relative to the straight longitudinal axis of said tubular structure to create an angled opening at said distal end, said angled distal end comprising a forward tip located at a distal portion of said angled distal end and a rearmost point located at a proximal portion of said angled distal end, said tubular structure having a longitudinal groove formed into an inner surface of said wall extending to said rearmost point at said angled distal end, said longitudinal groove being straight over its entire length; and
   An elongate instrument having a proximal end a distal end, said distal end having a distal tip sized to fit within said longitudinal groove of said conduit;
   wherein said longitudinal groove is capable of guiding said distal tip of said elongate instrument to the blood vessel or target organ.

28. The kit of claim 27 wherein said longitudinal groove extends along the entire length of said hollow tubular structure.

29. The kit of claim 27 wherein said distal end has a contour configured to engage the surface of said blood vessel or said target organ.

30. The kit of claim 29 wherein said contour has a concave shape that matches the radial curvature on the outer surface of said vessel or said organ.

31. The kit of claim 29 wherein said angled distal end comprises a distal tip that is scooped out so as to conform to the surface of the blood vessel or target organ such that it will continue to engage said vessel or organ if said access conduit is tilted upward to a greater angle than its intended angle of entry.

32. The kit of claim 27 wherein the cross-section of said longitudinal groove has a curvilinear shape.

33. The kit of claim 27 wherein said elongate instrument is a needle.

34. The kit of claim 27 wherein said elongate instrument is a light source.

35. The conduit of claim 1 wherein said open end at said proximal end comprises an opening encompassing the full cross sectional area internal to the conduit at said proximal end.

36. The conduit of claim 1 wherein said open end at said proximal end comprises an opening that faces the said straight longitudinal axis of said straight elongate tubular structure.

37. The conduit of claim 3 wherein said contour comprises a side-to-side curve to match the curve of the outer surface of said vessel or said organ.

38. The conduit of claim 9 wherein said open end at said proximal end comprises an opening encompassing the full cross sectional area internal to the conduit at said proximal end.

39. The conduit of claim 9 wherein said open end at said proximal end comprises an opening that faces the said straight longitudinal axis of said straight elongate tubular structure.

40. The conduit of claim 10 wherein said contour has a concave shape that matches the radial curvature on the outer surface of said vessel or said organ.

41. The kit of claim 27 wherein said open end at said proximal end comprises an opening encompassing the full cross sectional area internal to the conduit at said proximal end.

42. The kit of claim 27 wherein said open end at said proximal end comprises an opening that faces the said straight longitudinal axis of said straight elongate tubular structure.

43. A conduit for use in apparatus and methods for percutaneous access to blood vessels or other target organs in a human body comprising:
   a straight elongate hollow tubular structure sized to fit within a body cavity and to access a human body structure, said tubular structure being open at both ends and having a proximal end and a distal end;
   said tubular structure comprising a circumferential wall having an inner surface and an outer surface, a first longitudinal access channel of a first diameter and a second longitudinal guide channel of a second diameter less than said first diameter;
   said guide channel being formed as a longitudinal groove into said inner surface of said access channel such that said guide channel is open to said access channel along its entire length, such that said circumferential wall encloses both said first longitudinal access channel and said second longitudinal guide channel, said guide channel being straight over its entire length and extending to said distal end;
   wherein said open distal end is angled from 20 to 80 degrees relative to the straight longitudinal axis of said tubular structure to create an angled opening at said distal end, said angled distal end comprising a forward tip located at a distal portion of said angled distal end and a rearmost point located at a proximal portion of said angled distal end, and said longitudinal groove extends to said rearmost point at said angled distal end.

44. The conduit of claim 43 wherein said guide channel is formed as a longitudinal protuberance of said circumferential wall.

45. The conduit of claim 43 wherein said circumferential wall is circumferentially continuous.

46. The conduit of claim 43 wherein said circumferential wall is translucent and transmits light.

47. The conduit of claim 43 wherein said tubular structure further comprises a wall having an inner surface and an outer surface, said wall being of unitary construction along its entire length.

48. The conduit of claim 43 wherein said distal end has a contour configured to engage the surface of the blood vessel or other target organ.

49. The conduit of claim 48 wherein said contour has a concave shape that matches the radial curvature on the outer surface of said vessel or said organ.

50. The conduit of claim 43 wherein said tubular structure possesses at the most distal point of its distal end a localized change in contour adapted to interface with a generally cylindrical blood vessel.

51. The conduit of claim 43 wherein the cross-section of said longitudinal groove has a curvilinear shape.

52. The conduit of claim 43 wherein said open end at said proximal end comprises an opening encompassing the full cross sectional area internal to the conduit at said distal end.

53. The conduit of claim 43 wherein said open end at said proximal end comprises an opening that is directed along said straight longitudinal axis of said straight elongate tubular structure.

54. The conduit of claim 1 further comprising a circumferential wall enclosing an inner passageway, wherein said longitudinal groove is formed as a longitudinal protuberance of said circumferential wall.

55. The conduit of claim 9
    wherein said longitudinal groove extends along the entire length of said inner surface from said rearmost point of said angled distal end to said proximal end of said hollow tubular structure.

56. The conduit of claim 43
    wherein said longitudinal groove extends along the entire length of said inner surface from said rearmost point of said angled distal end to said proximal end of said hollow tubular structure.

57. The conduit of claim 1 wherein said blood vessel is the femoral artery and said tubular structure is sized to match the diameter of said femoral artery.

58. The conduit of claim 15 wherein said blood vessel is the femoral artery and said tubular structure is sized to match the diameter of said femoral artery.

59. The conduit of claim 43 wherein said blood vessel is the femoral artery and said tubular structure is sized to match the diameter of said femoral artery.

* * * * *